(12) United States Patent
Lee et al.

(10) Patent No.: US 8,048,541 B2
(45) Date of Patent: Nov. 1, 2011

(54) ORGANIC ELECTROLUMINESCENCE DEVICE

(75) Inventors: Shuit-Tong Lee, Hong Kong (HK);
Chun Sing Lee, Hong Kong (HK);
Pengfei Wang, Hong Kong (HK);
Zhiyuan Xie, Hong Kong (HK)

(73) Assignee: City University of Hong Kong, Kowloon Tong, Kowloon (HK)

( * ) Notice: Subject to any disclaimer, the term of this patent is extended or adjusted under 35 U.S.C. 154(b) by 210 days.

(21) Appl. No.: 12/336,734

(22) Filed: Dec. 17, 2008

(65) Prior Publication Data

US 2010/0148662 A1    Jun. 17, 2010

(51) Int. Cl.
*H01L 51/50* (2006.01)

(52) U.S. Cl. ........ 428/690; 313/504; 313/505; 313/506; 544/234

(58) Field of Classification Search .................. 428/690; 313/504, 505, 506; 544/234
See application file for complete search history.

(56) References Cited

U.S. PATENT DOCUMENTS

| | | | |
|---|---|---|---|
| 3,172,862 A | 3/1965 | Gurnee et al. | |
| 3,173,050 A | 3/1965 | Gurnee | |
| 4,539,507 A | 9/1985 | VanSlyke et al. | |
| 4,885,211 A | 12/1989 | Tang et al. | |
| 5,059,862 A | 10/1991 | VanSlyke et al. | |
| 5,069,975 A | 12/1991 | Nakada et al. | |
| 5,104,740 A | 4/1992 | Shinkai et al. | |
| 5,126,214 A | 6/1992 | Tokailin et al. | |
| 5,141,671 A | 8/1992 | Bryan et al. | |
| 5,389,444 A | 2/1995 | Hosokawa et al. | |
| 5,593,788 A | 1/1997 | Shi et al. | |
| 5,935,720 A | 8/1999 | Chen et al. | |
| 5,972,247 A | 10/1999 | Shi et al. | |
| 6,020,078 A | 2/2000 | Chen et al. | |
| 6,245,449 B1 | 6/2001 | Tamano et al. | |

OTHER PUBLICATIONS

Xu Tu-hong et. al., New red organic electroluminescent materials based on neutral red, 2007, J. Of Functional Materials and Devices, vol. 13, No. 1, pp. 39-43.*
Lee et. al., A Novel Neutral Red Derivative . . . Electroluminscent Devices, 2003, Chemical Materials, vol. 15, pp. 1913-1917.*
Neher et. al., Influence of dopant conc . . . hole-transporting alignment layers . . . , 2002, Polymers, vol. 43, pp. 5235-5242.*

* cited by examiner

*Primary Examiner* — Jennifer Chriss
*Assistant Examiner* — Gregory Clark
(74) *Attorney, Agent, or Firm* — Leydig, Voit & Mayer, Ltd.

(57) ABSTRACT

An electroluminescence device has an anode, a cathode and an emitting layer located between the anode and the cathode. The emitting layer contains a compound selected from a group consisting of neutral red and its derivatives.

10 Claims, 1 Drawing Sheet

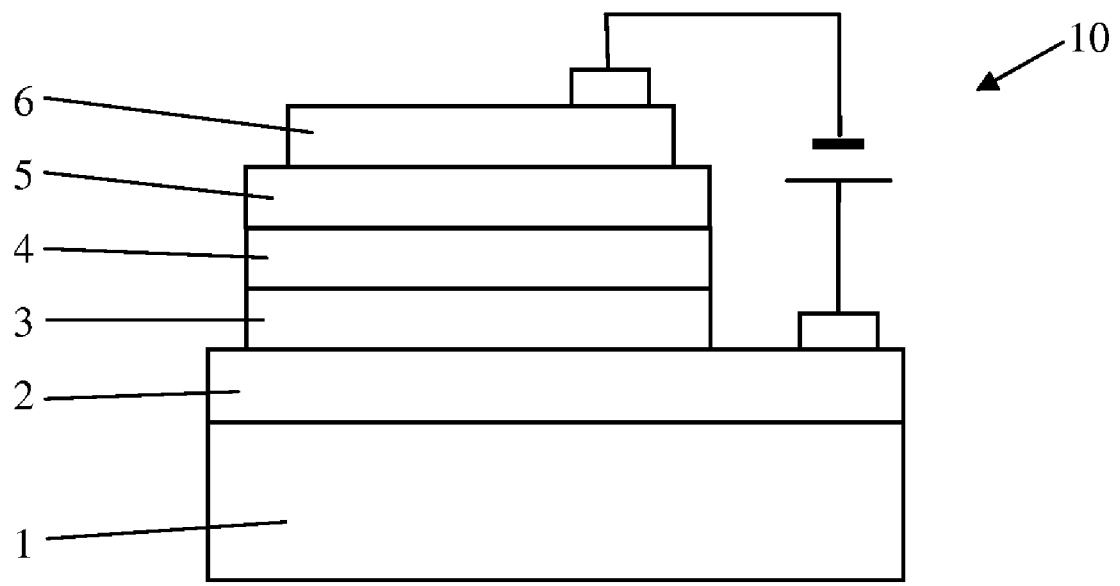

ORGANIC ELECTROLUMINESCENCE DEVICE

FIELD OF THE INVENTION

This invention relates to organic electroluminescence (EL) devices.

BACKGROUND OF THE INVENTION

U.S. Pat. Nos. 3,172,862, and 3,173,050 both granted in the 1965 teach the preparation of an organic electroluminescence (EL) device using conjugated materials generally having a fused aromatic ring. The efficiency and life of such organic EL devices was much lower than those obtained from inorganic systems. Therefore, research at that time was mainly focused on inorganic materials. The reason for the low luminance of early organic EL devices was the highly resistive EL medium, which prevented the efficient injection and transport of charge carriers into the light-emitting layer. Tang and VanSlyke (Tang and VanSlyke, Appl. Phys. Lett. 1987, 51, 913) solved this problem successfully in the late 1980s by using a structure made of two ultra thin layers: a hole transporting layer of an organic substance laminated on an organic emitting layer. This work revived the research into organic EL devices and resulted in the development of a new generation of light-emitting diodes based on organic dyes. Since then, much work has been done to further improve the efficiency, stability, color purity and so forth of such devices. One improvement was to dope a strong emitting material into a host material to form a guest-host system. Thus, in principle, an organic EL device with good efficiency and high stability, as well as desired color with proper chromaticity, could be obtained by doping different strongly emitting materials into a host material such as tri-(8-hydroxyquinolinato)aluminum ($Alq_3$) to meet the requirement of the practical applications. As a general rule, the energy gap between the lowest unoccupied molecular orbital (LUMO) and the highest occupied molecular orbital (HOMO) of a host material should be larger than that of the doped guest material to allow an efficient energy transfer from the host to guest.

$Alq_3$ is one of the most widely used host materials in organic EL devices. Its use as a host material for a green-emitting device and a red-emitting device made of DCM derivatives is ought in U.S. Pat. Nos. 5,593,788 and 5,935,720 respectively. The guest material, or dopant, that emits at longer wavelengths, such as green, yellow and red region can be, for example, compounds with large fused homo-aromatic rings or intramolecular charge transfer (ICT) compounds with electron donating (D) groups and electron withdrawing groups (A) linked by a conjugated structure. Since the fused homo-aromatic compounds with a large conjugated structure, especially those that emit in red, are often oxidized easily by singlet oxygen in ambient conditions they are not suitable dopants unless the EL devices are used in the dark or without oxygen. Compared with the fused homo-aromatic rings compounds, ICT compounds have the following advantages:

(i) The emission wavelength can be easily tuned by changing substitutes to obtain different colors.

(ii) The molecular structure is relatively easy to modify for desired properties.

(iii) Their Stokes shifts are generally large to prevent efficient self-re-absorption, especially in the solid state.

(iv) They are chemically stable, not easily oxidized by singlet oxygen.

SUMMARY OF THE INVENTION

In the current invention Neutral red and its derivatives are used as the guest material of dopant. Neutral red and its derivatives are a kind of the phenazine dyes. Most neutral red derivatives are strongly fluorescent in longer wavelengths such as the orange-red region. The neutral red derivatives in the present invention are typical ICT compounds, so these compounds are expected to have the general features of ICT compounds mentioned above. Moreover, they have an additional feature of high fluorescence and have a narrow emission band due to the totally rigid structure between the donor and accepter resulting in an organic EL device with improved efficiency and high brightness.

According to a particular aspect the invention provides an organic EL device comprising an anode, a cathode, a hole transport layer, an electron layer, and at least one organic emitting layer containing a compound of formula (I)-(V).

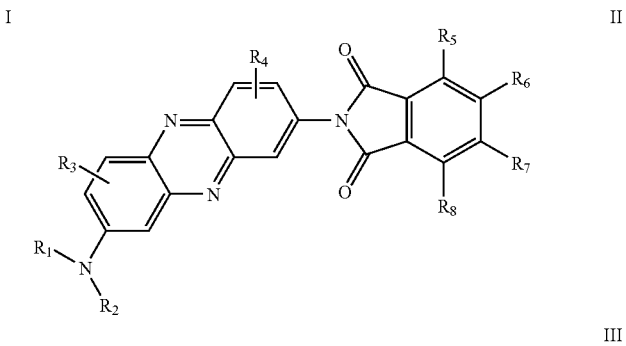

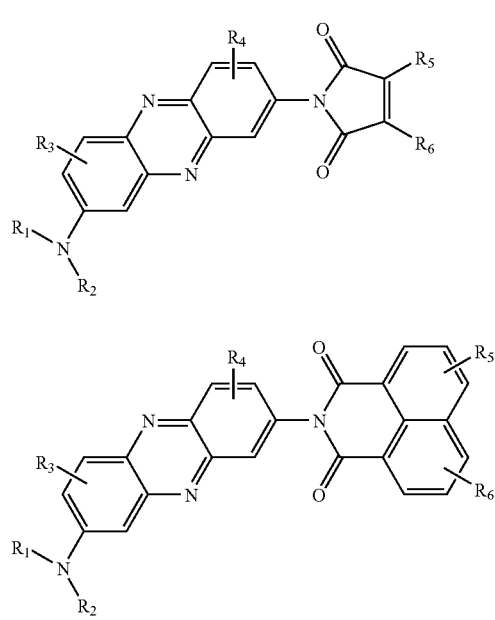

-continued

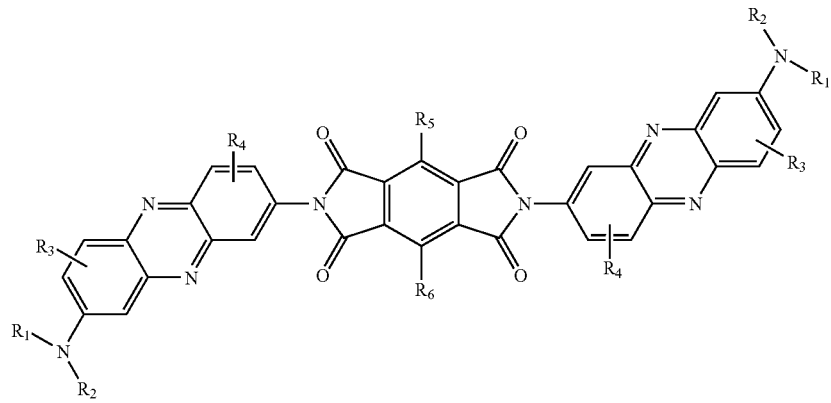

IV

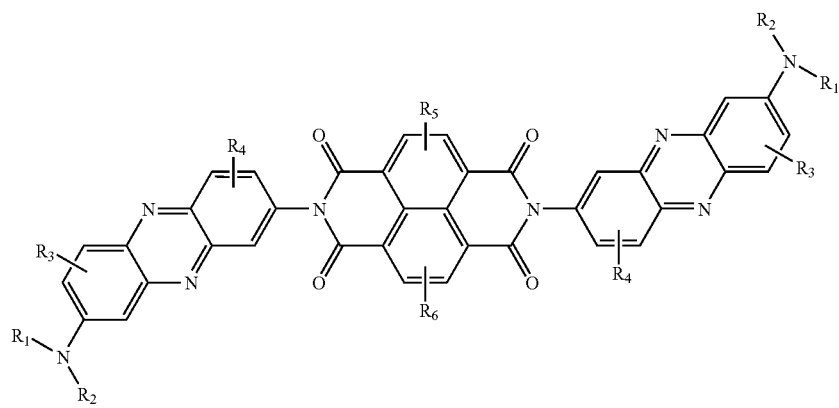

V

In structures (I), (II), (IV), (V), each $R_1$-$R_8$ is selected independently from the groups consisting of hydrogen, halogen, cyano, nitro, carbonyl, sulfone, ester, alkoxy, alkyl, alkylamino, dialkylamino, arylamino, diarylamino, haloalkyl containing a lower alkyl, hydroxyalkyl containing a lower alkyl, styryl, alkoxyl, alkyloxy, alkylthio, aryloxy, arylthio, siloxy, aryl or substituted aryl, substituted or unsubstituted heterocyclic hydrocarbons.

In structures (III), each $R_1$-$R_8$ is selected independently from the groups consisting of halogen, cyano, nitro, carbonyl, sulfone, ester, alkoxy, alkyl, alkylamino, dialkylamino, arylamino, diarylamino, haloalkyl containing a lower alkyl, hydroxyalkyl containing a lower alkyl, styryl, alkoxyl, alkyloxy, alkylthio, aryloxy, arylthio, siloxy, aryl or substituted aryl, substituted or unsubstituted heterocyclic hydrocarbons, except for hydrogen.

An organic EL device of the invention has high efficiency and narrow emission band. For example, when one derivative is doped into $Alq_3$, it gives a very bright yellow, orange to red emission depending on the doping concentrations. The device with a doping concentration 1% (wt %) exhibited a maximum brightness of 21800 $cd/m^2$ at a driving voltage of 12 V, and the current efficiency is 6.2 cd/A at a current density of 20 $mA/cm^2$; a orange emission from the doped emitting material with maximum wavelength 586 nm, and an red emission at high doping concentrations with maximum wavelength 612 nm. In particular, the device shows that the current efficiencies remain almost flat for a wide range of current density from 1 $mA/cm^2$ to 500 $mA/cm^2$ at different doping concentrations. The current devices show obvious advantages over many reported red-emitting OLEDs which show significant drops in efficiency as increasing current density and/or dopant concentration. The present dopant is particularly suitable for the passive-matrix displays application where a high excitation density is required. Furthermore, the materials provided by the invention are easy to prepare, and thus are economically attractive.

BRIEF DESCRIPTION OF THE DRAWINGS

The invention will now be described in more detail with reference to the accompanying drawing, which is a schematic diagram of the structure of the organic EL device of the present invention.

DETAILED DESCRIPTION OF THE PREFERRED EMBODIMENTS

The accompanying drawing illustrates the structure of an organic EL device 10. The layered structure comprising a base substrate 1; an anode electrode 2; an organic hole transport layer 3; an organic emitting layer 4; an organic electron transport layer 5 and a cathode electrode 6.

The substrate 1 is used as a support for the organic electroluminescence device of the present invention. It can consist of a quartz or glass sheet, a metal sheet or foil, or a plastic film or sheet. The preferred materials are glass sheet or transparent synthetic resin, such as polyester, polycarbonate, and polysulfone.

The anode 2 is located on the substrate 1 and is usually made of a metal such as silver, gold, aluminum, nickel, palladium, a metal oxide such as an oxide of indium and/or tin, carbon black or a conductive resin such as poly(3-methylthiophene). The cathode 6 can be made of the same material as the anode 2, but is preferably a metal with low work function, which is conducive to the efficient injection of electrons. Suitable cathode metals include magnesium, aluminum, silver, indium, or their alloys. The anode 2 and cathode 6 are prepared by vacuum deposition or sputtering. However, when the material is the fine particles of a metal, carbon black, a metal oxide or conductive resin powder, it can be dispersed into a suitable binder resin in solution and coated on a substrate to form the electrodes. In the case of a conductive resin, a thin film may be formed directly on a substrate by electrolytic polymerization. The anode 2 or cathode 6 can be made to have a multilayered structure by depositing of different materials. However, at least one of the electrodes 2, 6 must transmit visible light to a required degree: usually at least 60%, but preferably at least 80%. In this respect, the layer should not be too thick, generally from 5-1,000 nm, and preferably 10-500 nm.

An organic hole-transporting layer 3 is located on the anode 2. The hole-transporting layer 3 generally consists of a compound that is able to transport holes efficiently from the anode 2 to the organic emitting layer 4 between the electrodes 2, 6 to which an electric field is applied. Therefore, such a compound is required to be highly efficient at injecting holes from the anode 2. It must be capable of efficiently transporting the injected holes to an emitting layer 4 or an emitting material, preventing the migration of excitons generated in an emitting layer into an electron injecting zone or an electron transporting material, and highly capable of forming a thin film. Thus, in this respect, a suitable hole-transporting compound usually should have a low ionization potential, large hole mobility and stability. Moreover, the impurities likely to form traps should be avoided as far as possible. Examples of materials known to be useful as hole transporting materials, either combined or separately, are disclosed in U.S. Pat. No. 5,935,720 and include phthalocyanine derivatives, naphthalocyanine derivatives, porphyrin derivatives, pyrazoline derivatives, carbazole derivatives, polymer materials such as polyvinylcarbazole, polysilane.

In the organic electroluminescence device 10 of the present invention, effective hole transporting materials preferably include an aromatic tertiary amine derivative. Exemplary suitable hole-transporting materials are fully described by Y. Shirota in *J. Mater. Chem.*, 10, 1-25 (2000) and are illustrated as follows:

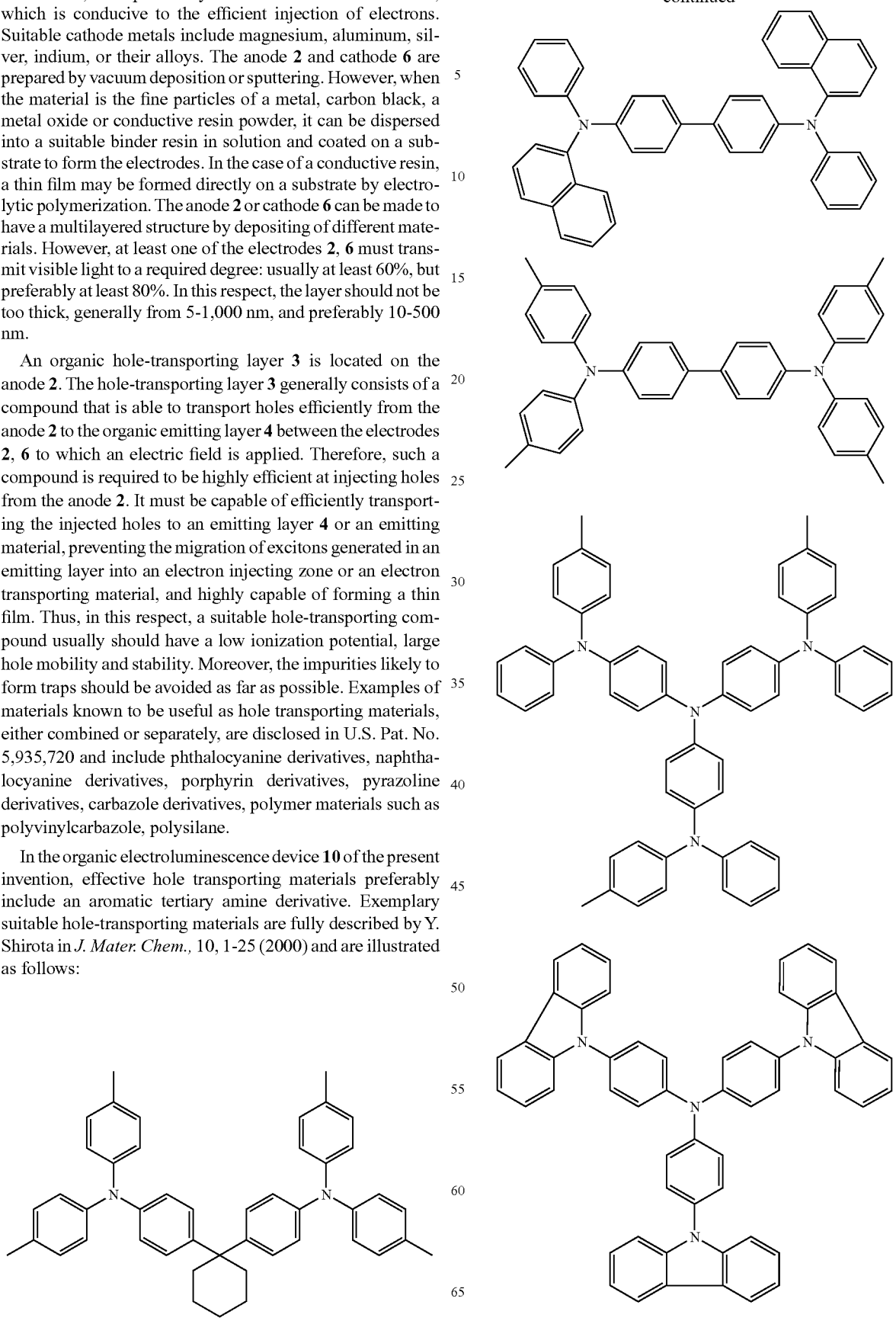

The hole transporting materials can be laminated on anode 2 by a vacuum deposition method or a coating/casting method to form the organic hole transport layer 3. This hole transport layer usually has a thickness of from 5-400 nm, preferably from 30-100 nm. In order to obtain a thin film uniformly, the vacuum deposition method is preferred.

The organic electron transporting layer 5 should be a material into which electrons from cathode 6 can be injected easily, which has excellent electron transport mobility, and which blocks the migration of excitons generated in the light-emitting layer 4 into hole injection zone. Moreover, a good ability to form a thin film is desirable. Useful electron transport materials generally have a large electron affinity, such as, thiopyrandioxide derivatives, perylene tetracarboxylic acid derivatives, oxadiazole derivatives, metal complexes of 8-hydroxyquinoline, 10-hydroxybenzo[h]quinoline, pyrrolopyridine derivatives, naphthylidine derivatives. Several examples, which are also disclosed by Y. Shirota in *J. Mater. Chem.*, 10, 1-25 (2000), and Chen, Shi and Tang in *Macromol. Symp.*, 125, 1 (1997), are illustrated as follows:

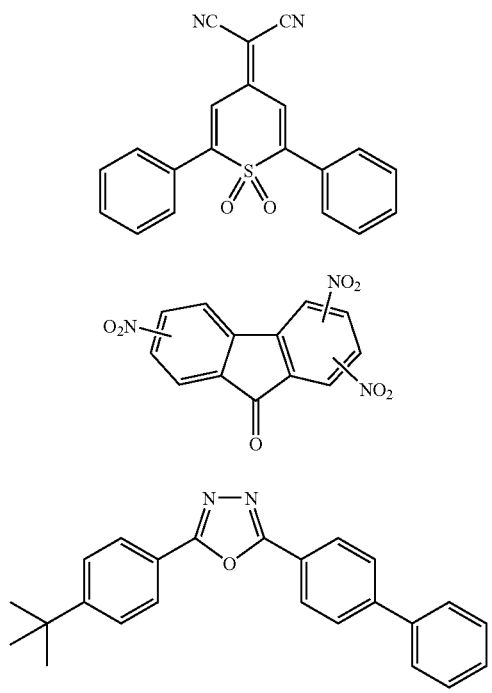

-continued

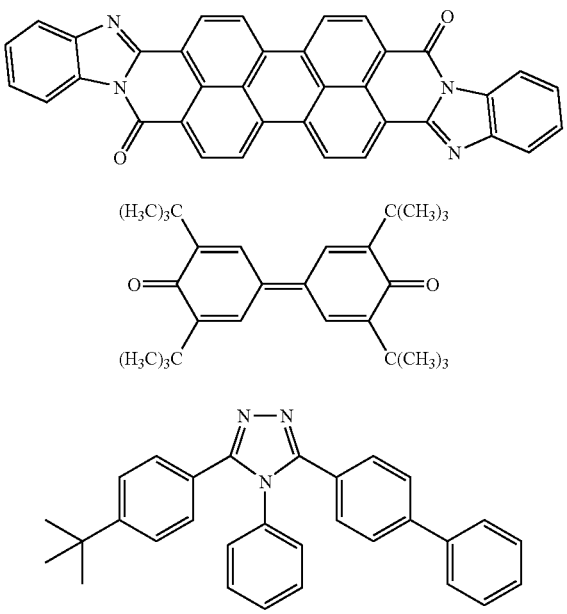

Electron transport layer 5 can be formed by a vacuum deposition method or a coating/casting method. This electron transport layer 5 usually has a thickness of from 5-400 nm, preferably from 30-100 nm. In order to obtain a thin film uniformly, the vacuum deposition method is preferred.

Organic light-emitting layer 4 of the present invention comprises a light-emitting material wherein electroluminescence is produced as a result of electron-hole recombination in this region. This electron-hole recombination produces excitons, which may decay to the ground state in a radiative way, resulting in an emission—fluorescence or phosphorescence. The light emitting materials is generally required to have a high emission quantum yield, a suitable energy gap, as well as a good ability to form a thin film uniformly. Materials for the emitting layer include the fused aromatic compounds, 8-hydroxyquinolinato metal complexes, such as $Alq_3$, as well as other fluorescence or phosphorescence dyes. The preferred embodiment $Alq_3$ is used. The organic light emitting material is doped with neutral red derivatives.

Neutral red derivatives with the following formula [I]-[V] have proved to be highly capable of improving the efficiency and performance.

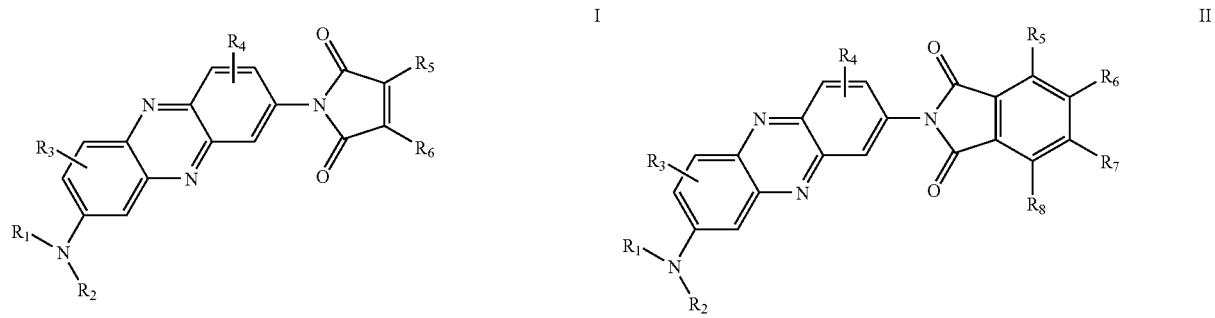

-continued

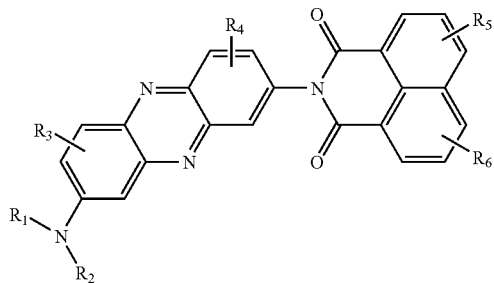

III

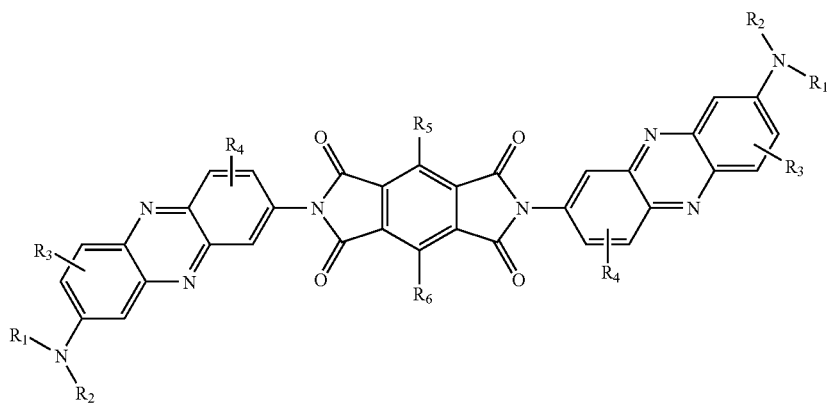

IV

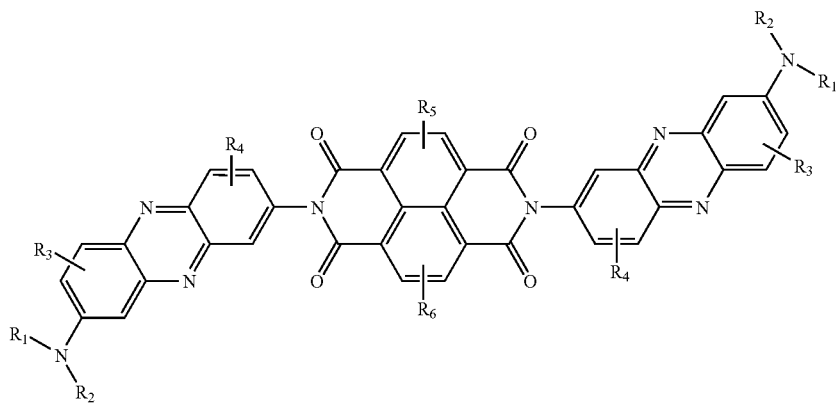

V

In formulae (I), (II), (IV), (V), each $R_1$-$R_8$ is independently hydrogen, halogen, cyano, nitro, carbonyl, sulfone, ester, alkoxy, alkyl, alkylamino, dialkylamino, arylamino, diarylamino, haloalkyl containing a lower alkyl, hydroxyalkyl containing a lower alkyl, styryl, alkoxyl, alkyloxy, alkylthio, aryloxy, arylthio, siloxy, aryl or substituted aryl, substituted or unsubstituted heterocyclic hydrocarbons. "Alkyl" refers to saturated hydrocarbon redifues containing eighteen or fewer carbons in straight or branched chains, as well as cyclic structures. "Lower alkyl" refers to those containing from 1-4 carbon atoms. "Aryl" means an aromatic hydrocarbon of 4 to about 16 carbon atoms. The term "heterocyclic hydrocarbon" means an unsaturated cyclic residue with 1-16 carbon atoms and 1-4 heteroatoms chosen from the group consisting of nitrogen, oxygen and sulfur.

In formulae (III), each $R_1$-$R_6$ is independently hydrogen, halogen, cyano, nitro, carbonyl, sulfone, ester, alkoxy, alkyl, alkylamino, dialkylamino, arylamino, diarylamino, haloalkyl containing a lower alkyl, hydroxyalkyl containing a lower alkyl, styryl, alkoxyl, alkyloxy, alkylthio, aryloxy, arylthio, siloxy, aryl or substituted aryl, substituted or unsubstituted heterocyclic hydrocarbons. "Alkyl" refers to saturated hydrocarbon redifues containing eighteen or fewer carbons in straight or branched chains, as well as cyclic structures. "Lower alkyl" refers to those containing from 1-4 carbon atoms. "Aryl" means an aromatic hydrocarbon of 4 to about 16 carbon atoms. The term "heterocyclic hydrocarbon" means an unsaturated cyclic residue with 1-16 carbon atoms and 1-4 heteroatoms chosen from the group consisting of nitrogen, oxygen and sulfur, except for hydrogen.

Examples of suitable alkyl groups containing from 1-18 carbon atoms include methyl, ethyl, propyl, butyl, sec-butyl, tert-butyl, pentyl, hexyl, heptyl, octyl, stearyl, and the like. Examples of alkyl amino residues include methyl amino, ethyl amino, propyl amino, butyl amino, sec-butyl amino, tert-butyl amino, pentyl amino, hexyl amino, heptyl amino, octyl amino, stearyl amino, and the like. Examples of dialkylamino groups include dimethyl amino, diethyl amino, dipropyl amino, dibutyl amino, disec-butyl amino, ditert-butyl amino, dipentyl amino, dihexyl amino, diheptyl amino, dioctyl amino, distearyl amino, and the like. Phenyl amino is an exemplary arylamino. Examples of diarylamino groups include diphenyl amino, phenylnaphthylamino, phenylanthrylamino, o-, p-, m-tolylnaphthylamino, o-, p-, m-tolylanthrylamino, naphthylanthrylamino, and the like. Examples of lower "haloalkyl" groups include chloromethyl, 3-chloropropyl, dichloromethyl, trichloromethyl, fluoromethyl, difluoromethyl, trifluoromethyl, and the like. Lower "hydroxyalkyl" residues include hydroxymethyl, hydroxyethyl, hydroxypropyl, and the like. "Alkyloxy" groups, also referred to as "alkoxyl", include methoxy, ethoxy, propoxy, butoxy, sec-butoxy, tert-butoxy, stearyloxy, and the like. Phenyloxy is an example of "aryloxy" residue. Examples of "alkylthio" substituents include methylthio, ethylthio, propylthio, butylthio, sec-butylthio, tert-butylthio, and the like. Phenylthio is an example of an "arylthio" group. Examples of substituted or unsubstituted "aryl" group containing only monocyclic hydrocarbons include phenyl, biphenylel, triphenylel, teraphenylel, o, m-, p-tolyl, xylyl. o-, m-, p-cumenyl, mesityl, and the like. Examplary fused polycyclic aryl group, substituted or unsubstituted, include pentarhenyl, indenyl, naphthyl, azulenyl, heptalenyl, acenaphtylenyl, phenalenyl, fluolenyl, anthryl, anthraquinonil, phenantolyl, pyrenyl, crysenyl, picenyl, rebicenyl, trinaphthylenyl, and the like. "Heterocyclic hydrocarbons", substituted or unsubstituted, include pyranthrenyl, oparenyl, thienyl, furyl, pyrrolyl, imidazolyl, pyrazolyl, pyridyl, pylazinyl, pyrimidinyl, pyridazinyl, indolyl, quinolyl, isoquinolyl, phthalazinyl, quinoxalynyl, quinazolynyl, carbazolyl, acrydinyl, phenadinyl, furluryl, isochiazolyl, isothiazolyl, isoquixazolyl, furazanyl, phenoquisadinyl, benzthiazolyl, benzoxazlyl, benzoimidazolyl, and the like.

The molecular structure for specially exemplary dopant used in the present invention are as follow:

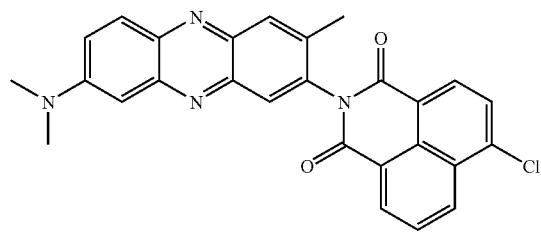

1

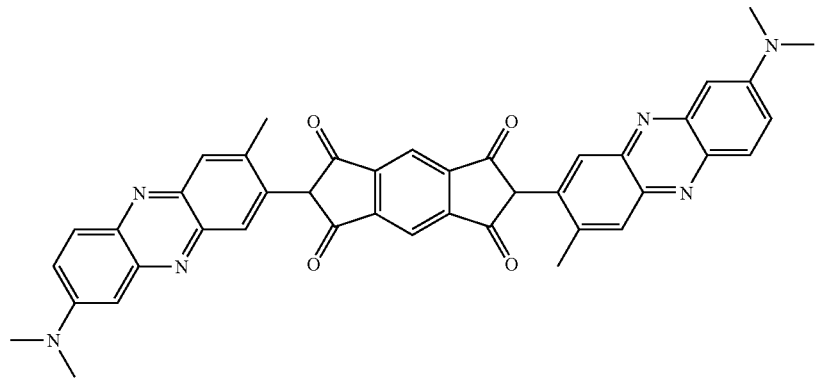

2

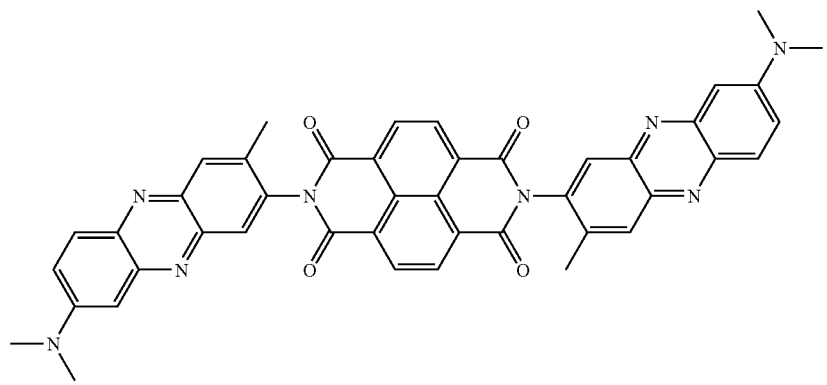

3

As a variation of the embodiment shown in FIG. 1, a thin layer, preferably about 15 nm thick, of hole injection material (not shown) such as copper phthalocyanine, porphyrinic derivatives disclosed in U.S. Pat. No. 5,972,247 can be inserted between the anode 2 and hole transporting layer 3 to enhance the hole injection from the anode 2 in an organic electroluminescence device. It should also be noted that the multi-component material of layer 4 may also be the hole transport material or the electron transport material, instead of a separated emission layer.

EXAMPLES

The present invention will be explained in more detail in the following examples, which are for illustrative purposes only and are not intended to limit the scope of use of the invention. Unless otherwise indicated, the reactants and reagents used in the reactions are readily available materials known in the art. Such materials can be conveniently prepared in accordance with conventional preparatory procedures or obtained from commercial sources.

Example 1

Synthesis of Neutral Red Derivative Compound 1

0.25 g Neutral red and 0.2 g 4-chloro-1,8-naphthalic anhydride were suspended in 20 ml quinoline. The mixture was refluxed for 24 hrs. at 220° C. under nitrogen. After cooling, the solution was poured into 50 ml ethanol. A red precipitate was collected, purified by recrystalization from ethanol; after dryness, 0.32 g deep red needles were obtained. $^1$HNMR (300 MHz, CDCl$_3$) δ [ppm]: 2.43 (s, 3H), 3.23 (s, 6H), 7.07 (d, J=3.0 Hz, 1H), 7.62-7.65 (m, 1H), 7.83-7.88 (m, 2H), 8.01-8.15 (m, 2H), 8.33-8.36 (m, 2H), 8.71-8.74 (m, 2H); Anal. Calcd. For C$_{27}$H$_{19}$Cl N$_4$O$_2$: C, 69.45; H, 4.10; N, 12.00%. Found: C, 69.63; H, 4.35; N, 12.19%; MS: m/z 467 (M$^+$+1).

Table 1 lists the absorption and emission maxima and fluorescence quantum yields of compound 1 in a variety of solvents. A red shift in the absorption and emission maxima was observed with increasing solvent polarity. The fluorescence quantum yield of compound 1 reveals a significant dependence on the solvent polarity, The fluorescence quantum yield of compound 1 decreases from almost unity in a non-polar solvent-n-heptane to 0.38 in a strongly polar solvent—acetonitrile. This result indicates a strong ICT character of the molecule in the excited state.

TABLE 1

Spectral and photophysical data of compound I at room temperature; $^a$DCM: dichloromethane, $^b$AN: acetonitrile.

| Solvents | n-Heptane | DCM$^a$ | AN$^b$ | MeOH |
|---|---|---|---|---|
| E$_T$(30) (Kcal/mol) | 30.8 | 41.1 | 46.0 | 55.5 |
| λ$^{ab.}_{max}$ (nm) | 462 | 479 | 495 | 512 |
| ε (dm$^3$ mol$^{-1}$ cm$^{-1}$) | 15430 | 14720 | 16120 | 17230 |
| λ$^{em.}_{max}$ (nm) | 514 | 575 | 594 | 599 |
| Φ$_f$ | ~1 | 0.77 | 0.38 | 0.10 |

Example 2

Synthesis of Neutral Red Derivative Compound 2

0.35 g Neutral red and 0.1 g 1,2,4,5-benzenetetracarboxylic anhydride were suspended in 20 ml quinoline. The mixture was refluxed for 48 hrs. at 220° C. under nitrogen. After cooling, the solution was poured into 50 ml ethanol. A red precipitate was collected, purified by re-crystallization from ethanol; after dryness, 0.18 g deep red solid were obtained. Anal. Calcd. For C$_{40}$H$_{30}$N$_8$O$_4$: C, 69.96; H, 4.40; N, 16.32%. Found: C, 69.86; H, 4.56; N, 16.59%; MS: m/z 687 (M$^+$+1).

Example 3

Synthesis of Neutral Red Derivative Compound 3

0.25 g Neutral red and 0.1 g Naphthalene-1,4,5,8-tetracarbolxylic dianhydride were suspended in 20 ml quinoline. The mixture was refluxed for 48 hrs. at 220° C. under nitrogen. After cooling, the solution was poured into 50 ml ethanol. A red precipitate was collected, purified by recrystalization from ethanol; after dryness, 0.22 g black red solid were obtained. Anal. Calcd. For C$_{44}$H$_{32}$N$_8$O$_4$: C, 71.73; H, 4.38; N, 15.21%. Found: C, 71.83; H, 4.65; N, 15.59%; MS: m/z 737 (M$^+$+1).

Electroluminescence Device Fabrication

The detailed results of electroluminescence (EL) are indicated in the following specific examples of the present invention. It is evident that the EL devices shows very bright orange to red emission with high efficiencies and relatively narrow emission band, and the current efficiencies of EL devices remain almost unchanged in a wide range of drive current density up to 500 mA at different doping concentrations, which is particularly desirable for the passive-matrix display application.

Example 4

An indium-tin-dioxide (ITO) coated glass substrate was sequentially ultrasonicated in a detergent, rinsed in deionized water, exposed to UV light for 20 minutes and dried. A hole transporting layer 3 of N,N'-bis-(1-naphthyl)-N,N'-diphenyl-benzidine was deposited on ITO anode at the vacuum deposition rate of about 15 nm/min. by using a tantalum boat to form a thickness of 60 nm. A light-emitting layer 4 of Alq$_3$ doped with a material with formulae [I]-[V] was then co-deposited onto the hole-transporting layer 3 with a thickness of about 30 nm. The concentration of dopants can be controlled by deposition rate as required. An electron-transporting layer 5 of Alq$_3$ was deposited onto the light-emitting layer 4 with a thickness of about 30 nm. A cathode 6 consisting of a 10/1 atomic ratio of Mg/Ag was deposited onto the Alq$_3$ layer 5 with a thickness of about 200 nm. The device was hermetically packaged in a dry glove box.

Example 5

The electroluminescence device with compound (1) doped AlQ$_3$ as the light-emitting layer was fabricated by following the same procedure as in Example 4. The light emission characteristics were listed in Table 2, and also shown as follows: a maximum brightness of 21800 cd/m$^2$ at a driving voltage of 12 V, and the current efficiency is 6.2 cd/A at a current density of 20 mA/cm$^2$; a orange emission from the doped emitting material with maximum wavelength 586 nm, and an red emission at high doping concentrations with maximum wavelength 612 nm.

TABLE 2

EL performances of compound-doped devices with structure of NPB(60 nm)/Alq$_3$:dopant (25 nm)/Alq$_3$(30 nm).

| Doping concentration | IP | EA | η$^{max.}$ | Devices performance at 20 mA/cm$^2$ | | |
|---|---|---|---|---|---|---|
| (wt %) | (eV) | (eV) | (cd/A) | L(cd/m$^2$) | η (cd/A) | λ (nm) |
| 0.5 | 5.4 | 3.1 | 5.4 | 1340 | 5.1 | 586 |
| 1.0 | | | 6.5 | 1800 | 6.2 | 586 |

TABLE 2-continued

EL performances of compound-doped devices with structure of
NPB(60 nm)/Alq₃:dopant (25 nm)/Alq₃(30 nm).

| Doping concentration (wt %) | IP (eV) | EA (eV) | $\eta^{max.}$ (cd/A) | Devices performance at 20 mA/cm² | | |
|---|---|---|---|---|---|---|
| | | | | L(cd/m²) | η (cd/A) | λ (nm) |
| 3.0 | | 3.5 | | 570 | 3.4 | 598 |
| 5.0 | | 1.3 | | 220 | 1.0 | 612 |

What is claimed is:

1. An electroluminescence device comprising an anode, a cathode, and an emitting layer located between the anode and the cathode, wherein the emitting layer contains a compound of formula I:

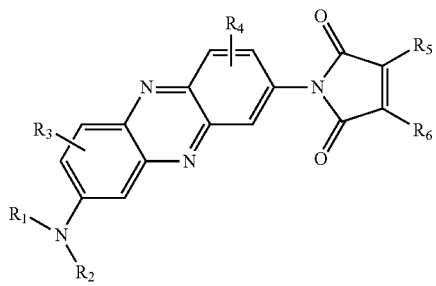

wherein $R_1$-$R_6$ are each independently selected from hydrogen, halogen, cyano, nitro, carbonyl, sulfone, ester, alkoxy, alkyl, alkylamino, dialkylamino, arylamino, diarylamino, haloalkyl containing a lower alkyl, hydroxyalkyl containing a lower alkyl, styryl, alkoxy, alkyloxy, alkylthio, aryloxy, arylthio, siloxy, aryl or substituted aryl, and substituted or unsubstituted heterocyclic hydrocarbons.

2. The electroluminescence device of claim 1 further comprising a hole transport layer adjacent to the anode and an electron transport layer adjacent to the cathode, wherein the emitting layer is located between the hole transport layer and the electron transport layer.

3. The electroluminescence device of claim 2, wherein the emitting layer comprises an organic light-emitting host material doped with the compound of formula I.

4. The electroluminescence device of claim 3 wherein the organic light-emitting host material is a fluorescent or phosphorescent compound.

5. An electroluminescence device comprising an anode, a cathode, and an emitting layer located between the anode and the cathode, wherein the emitting layer contains a compound of formula IV:

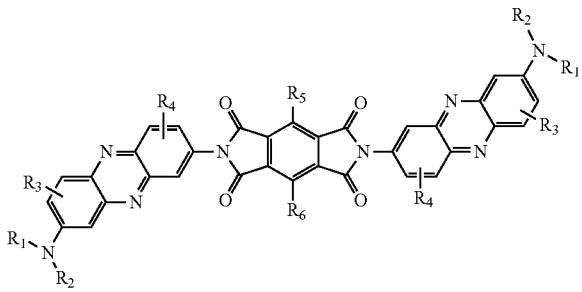

wherein $R_1$-$R_6$ are each independently selected from hydrogen, halogen, cyano, nitro, carbonyl, sulfone, ester, alkoxy, alkyl, alkylamino, dialkylamino, arylamino, diarylamino, haloalkyl containing a lower alkyl, hydroxyalkyl containing a lower alkyl, styryl, alkoxy, alkyloxy, alkylthio, aryloxy, arylthio, siloxy, aryl or substituted aryl, and substituted or unsubstituted heterocyclic hydrocarbons.

6. The electroluminescence device of claim 5 further comprising a hole transport layer adjacent to the anode and an electron transport layer adjacent to the cathode, wherein the emitting layer is located between the hole transport layer and the electron transport layer.

7. The electroluminescence device of claim 6, wherein the emitting layer comprises an organic light-emitting host material doped with the compound of formula IV.

8. The electroluminescence device of claim 7 wherein the organic light-emitting host material is a fluorescent or phosphorescent compound.

9. A method of making an electroluminescence device comprising an anode, a cathode, and an emitting layer located between the anode and the cathode, the method comprising:

doping the emitting layer with a compound of formula I:

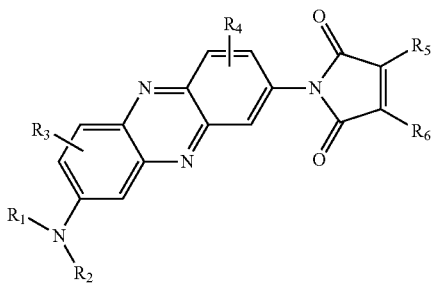

wherein $R_1$-$R_6$ are each independently selected from hydrogen, halogen, cyano, nitro, carbonyl, sulfone, ester, alkoxy, alkyl, alkylamino, dialkylamino, arylamino, diarylamino, haloalkyl containing a lower alkyl, hydroxyalkyl containing a lower alkyl, styryl, alkoxy, alkyloxy, alkylthio, aryloxy, arylthio, siloxy, aryl or substituted aryl, and substituted or unsubstituted heterocyclic hydrocarbons.

10. A method of making an electroluminescence device comprising an anode, a cathode, and an emitting layer located between the anode and the cathode, the method comprising:

doping the emitting layer with a compound of formula IV:

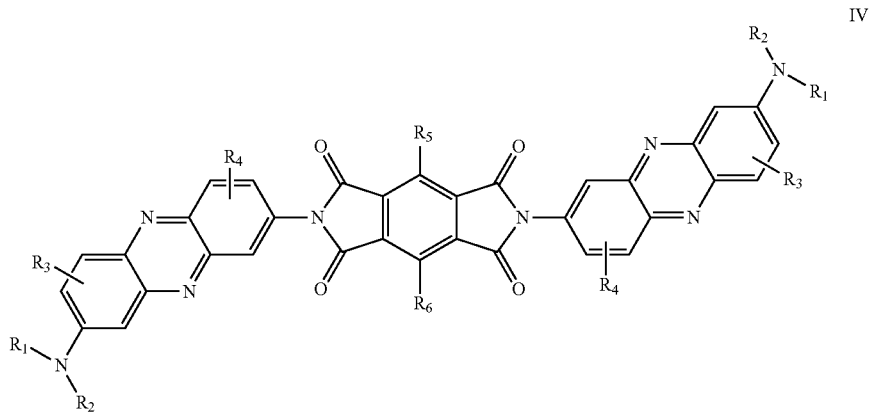

wherein $R_1$-$R_6$ are each independently selected from hydrogen, halogen, cyano, nitro, carbonyl, sulfone, ester, alkoxy, alkyl, alkylamino, dialkylamino, arylamino, diarylamino, haloalkyl containing a lower alkyl, hydroxyalkyl containing a lower alkyl, styryl, alkoxy, alkyloxy, alkylthio, aryloxy, arylthio, siloxy, aryl or substituted aryl, and substituted or unsubstituted heterocyclic hydrocarbons.

* * * * *